US009134248B2

(12) United States Patent
Meinhart et al.

(10) Patent No.: US 9,134,248 B2
(45) Date of Patent: Sep. 15, 2015

(54) SYSTEMS FOR ANALYTE DETECTION

(71) Applicant: OndaVia Inc., Hayward, CA (US)

(72) Inventors: Carl D. Meinhart, Santa Barbara, CA (US); Brian D. Piorek, Santa Barbara, CA (US); T.J. Reed, Santa Barbara, CA (US); Ian Cutler, Santa Barbara, CA (US); Philip Strong, Goleta, CA (US)

(73) Assignee: OndaVia, Inc., Hayward, CA (US)

( * ) Notice: Subject to any disclaimer, the term of this patent is extended or adjusted under 35 U.S.C. 154(b) by 0 days.

(21) Appl. No.: 13/688,184

(22) Filed: Nov. 28, 2012

(65) Prior Publication Data
US 2013/0244337 A1 Sep. 19, 2013

Related U.S. Application Data

(60) Provisional application No. 61/564,813, filed on Nov. 29, 2011.

(51) Int. Cl.
*G01N 21/65* (2006.01)
*G01N 33/00* (2006.01)
*G01N 15/06* (2006.01)
*B01L 3/00* (2006.01)

(52) U.S. Cl.
CPC ........ *G01N 21/658* (2013.01); *B01L 3/502715* (2013.01); *G01N 15/0606* (2013.01); *G01N 33/0011* (2013.01); *B01L 2200/16* (2013.01); *B01L 2300/0654* (2013.01); *B01L 2300/0816* (2013.01); *B01L 2300/0835* (2013.01); *B01L 2400/0406* (2013.01); *B01L 2400/049* (2013.01); *B01L 2400/0683* (2013.01); *G01N 2015/0693* (2013.01); *Y10T 29/301* (2015.01); *Y10T 29/49826* (2015.01)

(58) Field of Classification Search
CPC .................................................. G01N 21/658
USPC .......................................................... 422/554
See application file for complete search history.

(56) References Cited

U.S. PATENT DOCUMENTS

| 6,156,181 A * | 12/2000 | Parce et al. ................... 204/600 |
| 8,017,408 B2 | 9/2011 | Meinhart et al. |
| 2006/0163069 A1* | 7/2006 | Prak et al. ....................... 204/601 |
| 2008/0199851 A1* | 8/2008 | Egan et al. ......................... 435/5 |
| 2010/0143194 A1* | 6/2010 | Lee et al. ..................... 422/68.1 |

(Continued)

FOREIGN PATENT DOCUMENTS

| WO | WO 2010102194 | * | 9/2010 |
| WO | WO 2011/022400 A1 | | 2/2011 |
| WO | WO 2011/047199 A2 | | 4/2011 |
| WO | WO 2011/066512 A2 | | 6/2011 |

(Continued)

*Primary Examiner* — Lyle Alexander
*Assistant Examiner* — Emily Berkeley
(74) *Attorney, Agent, or Firm* — NUPAT, LLC; Morrison Ulman

(57) ABSTRACT

This disclosure provides a system component and method for analysis of airborne analytes by absorbing the analytes into a liquid and interrogating the liquid with an analytical instrument. In some examples, a cartridge with a microfluidic chip contains a vessel of a colloidal solution of nanostructured particles in a liquid. The vessel is broken, releasing the solution into microfluidic containers on the chip. Air having analytes is passed over the chip leading to absorption of airborne analytes into the solution. The analytes bind with the nanostructures and are detected optically. Techniques are disclosed for filling the vessel in a way that maintains the efficacy of the solution until it is needed for measurement.

9 Claims, 9 Drawing Sheets

(56) References Cited

U.S. PATENT DOCUMENTS

2010/0210029 A1* 8/2010 Meinhart et al. ............ 436/168
2012/0281210 A1 11/2012 Lee et al.

FOREIGN PATENT DOCUMENTS

WO WO 2012/061636 A2 5/2012
WO WO 2012/145434 A1 10/2012

* cited by examiner

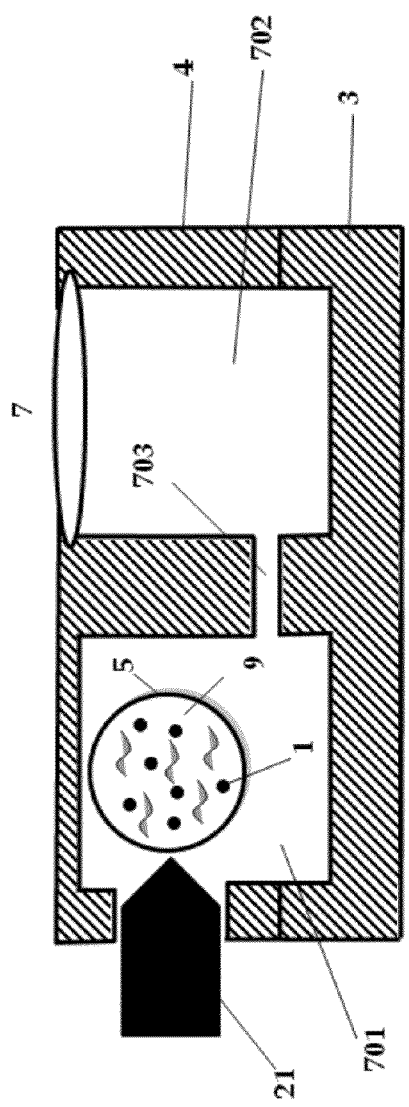
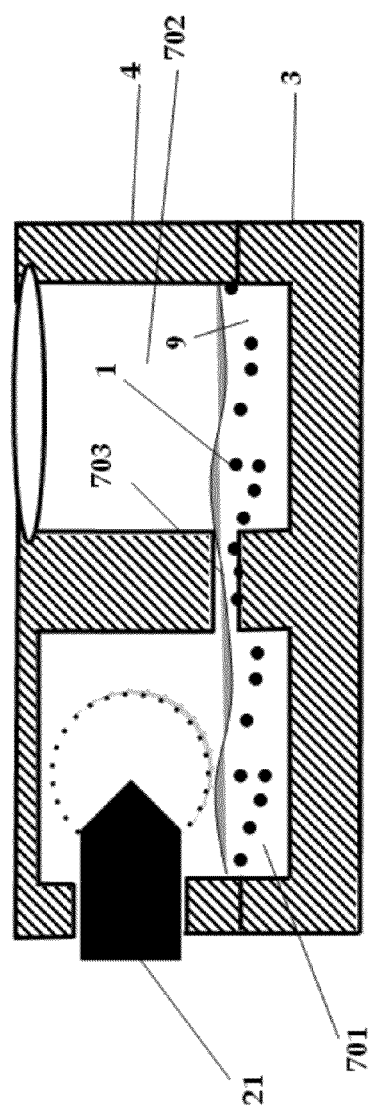

US 9,134,248 B2

SYSTEMS FOR ANALYTE DETECTION

CROSS-REFERENCE

This application claims priority to U.S. Provisional Patent Application Ser. No. 61/564,813, filed Nov. 29, 2011, which is entirely incorporated herein by reference.

BACKGROUND

Low concentrations of chemical species (analytes) targeted for detection and analysis pose technical challenges. Because low-concentration detection and analysis of some chemical compounds may necessitate large and heavy lab apparatus, field deployment is often rendered difficult or even impossible. In addition, the targeted analytes may be hazardous (e.g., toxic, explosive, or the like).

SUMMARY

The detection and identification of low concentration airborne agents has a number of benefits across a wide variety of vital applications, including the detection of explosives, drugs, infectious agents and toxic biomaterials, relating to anti-terrorism, drug enforcement and medical care, food inspection and other analytical chemistry applications. Because existing techniques for low-concentration detection and analysis of some chemical compounds necessitate complex and delicate lab apparatus, field deployment is often rendered difficult or impossible. In addition, the targeted analytes may be contaminated and/or mixed with false-positive compounds that confound accurate detection and analysis.

Low concentrations generally represent a low number density of analyte or target molecules and/or a high ratio of inert or untargeted compounds to the targeted compound(s), often necessitating a process of filtering or other concentrating processes, possibly with isolation or removal of contaminants. Existing processes used to isolate and concentrate analytes of interest prior to the detection/analytic process, are typically incompatible with field portability or real time detection techniques. There is a need for apparatus and processes that are both field portable and accurate, yielding minimal false-positive and false-negative detection events, and offering accurate and repeatable detection/analysis of the targeted analyte(s). Applications include hand-held chemical detectors for low-concentration vapor phase analytes such as drugs; explosives, chemical and/or biological agents potentially used in terrorist activities; and biological metabolites.

Technologies, systems, devices, or methods described herein can provide several elements in common. The first is that certain analytes in the gas phase in contact with a liquid surface will absorb into a liquid while others will not, depending on the hydrophillic/hydrophobic properties of the analyte with the liquid. For a given analyte of interest, a liquid may be chosen that selectively absorbs the target analyte while rejecting other gas-phase agents. A particularly useful example is that hydrophilic species, including common explosive compounds, can readily absorb into water, while non-polar hydrophobic molecules (e.g., gasoline, benzene and the like) do not. The physics of absorption and many examples of analyte/liquid combinations of interest are described in the incorporated references. For liquid bodies with a relatively large surface-to-volume ratio, even very low concentration of airborne analytes of interest may be captured in relatively small liquid volumes.

This disclosure provides devices, systems and methods for absorbing airborne chemical species into a liquid phase for analysis and identification.

According to certain aspects of the invention, once captured, these analytes are detected and analyzed. In very small volumes, relatively few analyte molecules are captured, so approaches for both detecting and identifying the analytes as well as building up a detectable concentration are disclosed herein and/or in references incorporated herein. A variety of analytical instruments may be used to analyze analytes in a liquid. In some aspects, a particularly useful implementation relies on the fact that if nanostructured elements, either the surfaces of liquid containers or suspended particles, are present in the liquid, some absorbed analytes will adhere to the nanostructured elements. If the liquid is interrogated with a Raman spectrometer, a phenomenon described as Surface Enhanced Ramam Spectrometry (SERS) occurs. This technique can increase the detectability of even very small concentrations of analyte by the amplification of the spectral emissions due to local electromagnetic (E/M) field effects around the nanostructures.

There are various techniques for taking advantage of such technologies. For example, some approaches to detection and identification of low concentration gas-phase analytes have been described by inventors common to the current application. At least some features of such techniques and systems are described in Patent Cooperation Treaty (PCT) Application No. PCT/US2010/34127; PCT/US2010/45761; PCT/US2010/052742; PCT/US2010/58234; PCT/US2011/059213; U.S. patent application Ser. No. 13/289,679; and U.S. Pat. No. 8,017,408 to Meinhart et al. ("Device and methods of detection of airborne agents"), each of which is incorporated herein by reference in its entirety. Such techniques perform well and form the basis for a variety of commercial instruments provided herein.

This disclosure provides a variety of applications and techniques using the technologies described herein. For instance, for some applications the liquid used for absorbing analytes can be a colloidal suspension of nanoparticles in a fluid of suitable characteristics. Such colloidal solutions are not commonly available and need to be produced specifically. For many possible applications of these techniques, particularly for field applications, such as drug and explosive detection, it is inconvenient to deliver prepared colloidal solutions to the measurement site. In some embodiments, very small quantities of such solutions are required for a given measurement cycle of absorption and spectroscopic interrogation.

In certain aspects, for each measurement cycle, only enough colloidal solution may be required to partially fill the channels or other geometry free-surface microfluidic containers in a typical "microfluidic chip" such as those described herein. In some embodiments, these containers have dimensions on the order of microns or millimeters, which provide a very high surface-to-volume ratio. As such, in some embodiments, only a relatively small amount of colloid is required. In some instances, particularly where measurements are of very high economic value, it is more desirable that the measurements be made reliably and conveniently than that they minimize cost per measurement. Thus, in some instances, it is possible to dispose of system components after each measurement, enabling a refreshed detection system to be utilized for each event. In some embodiments, the system components are disposable. In other embodiments, the disposable elements allow for rugged, reliable operation.

Provided herein are analyte capture and analysis techniques, systems, methods, devices, compositions, and the like having improved, practical field applications. An aspect of the invention described herein relates to the delivery of colloidal solution to the measurement environment, and/or improved technologies therefor.

This disclosure provides a cartridge or cartridge system for capturing and/or analyzing ambient gases and/or analytes in a gas or liquid suspected of having the ambient gases and/or analytes. A cartridge can include (i) a microfluidic chip, the microfluidic chip comprising at least one microfluidic container with at least one free surface, (ii) an optical window disposed for optical interrogation of the container (e.g., an unobstructed optical opening through which the container, or at least a portion thereof, may be irradiated), (iii) a colloid vessel chamber disposed in proximity to (e.g., adjacent to) the chip and at least one optional opening of the colloid vessel chamber in proximity to the container, (iv) an optional colloid vessel comprising a colloidal solution (e.g., if present the colloid vessel may be disposed in the colloid vessel chamber), the colloid solution comprising a liquid and nanostructured particles, and (v) an airflow manifold disposed for airflow across the chip. The free surface can include a free surface interface region that is open on at least one side to the gas or liquid having the ambient gases and/or analytes. In some embodiments, the system comprises a device or mechanism for releasing the contents of the vessel, such as, for example, by breaching the vessel (e.g., a valve in the vessel, or an instrument external to the vessel, such as an instrument to break a glass vessel or puncture a foil vessel). In some cases, during operation, the vessel is breached and colloidal solution fills the container. In some instances, airborne analytes are passed or otherwise directed over the container through the manifold and the interaction or reaction of absorbed airborne reagents with the nanostructured particles is detected optically.

In various detailed embodiments, the cartridge may also have an access port disposed to allow a vessel breaking tool to contact or otherwise open the vessel. In one embodiment, the vessel is an ampoule. The vessel (e.g., ampoule) may be made from any suitable material, such as a semiconductor (e.g., silicon, silicon oxide) containing material. In an example, the vessel is formed of glass, such as blown glass. The vessel or ampoule may have any suitable size, such as, for example, a spherical region 1-15 mm diameter and a fill tube region of length: 0.5-5 cm. In another embodiment, the vessel may be a foil packet, e.g., a metal packet 1-15 mm in size. In other examples, the vessel can be any container that is adapted to release the contents of the vessel when the vessel is unsealed or breached. The vessel can be formed of a breachable of friable material. In some situations, the application of heat, pressure or mechanical force to the vessel generates one or more openings in the vessel to release the contents of the vessel.

In some embodiments, the chip and cartridge body form at least one second container connected to the first by a constricted path. Upon breaking, the broken ampoule shards and colloidal solution fill the first chamber (e.g., a container) and capillary forces draw the colloidal solution, but not the shards, through the constricted path to the second chamber (e.g., a second microfluidic container as described herein). In some of such embodiments, absorption and optical detection takes place at the second chamber.

In another embodiment, provided herein is a process for delivering colloidal solution to a cartridge, where the cartridge is as described herein. In some embodiments, the cartridge comprises a chip with at least one microfluidic container with at least one free surface, an optical window to the container, an airflow manifold configured to direct air over the container, and a measuring system for detecting and/or measuring the presence of a gas phase and/or airborne analytes (e.g., a measuring system comprising a Raman spectrometer and a compartment for receiving the cartridge). In specific aspects, the process comprises the steps of (i) filling a vessel with a colloidal solution comprising liquid and nanostructured particles, (ii) loading the vessel in the cartridge (e.g., into the vessel chamber of the cartridge), such that the vessel is at least partially disposed in proximity to or adjacent to the microfluidic container, (iii) placing the cartridge in the measuring system with the optical window aligned with an optical component of the measuring system (e.g., placing the cartridge in the measuring system in such a manner so as to allow interrogation of the container through the optical window thereof using a Raman spectrometer of the measuring system), and (iv) breaching the vessel causing the colloidal solution to at least partially fill the container. Such steps are optionally employed in any suitable order. In certain aspects, the airborne reagents (gases, analytes, or the like) are passed over the vessel and/or through the manifold. In further embodiments, in detection and/or measurement processes, the interaction or reaction of the airborne reagents with the nanostructured particles may be observed (e.g., detected optically).

Also, provided herein is a system for detecting and/or measuring airborne ambient gases and/or analytes (e.g., using the delivery of a colloidal solution in a cartridge), the system comprising a cartridge as described herein or that comprises a chip with at least one microfluidic container with at least one free surface, an optical window to the container, an airflow manifold configured to direct air over the container, and a measuring system for detecting and/or measuring the presence of a gas phase and/or airborne analytes (e.g., a measuring system comprising a Raman spectrometer and a compartment for receiving the cartridge). Also provided in some embodiments is a process of detecting and/or measuring airborne ambient gases and/or analytes (e.g., using the delivery of a colloidal solution in a cartridge), using a cartridge or system described herein and having the steps of (i)-(iv) as described above and further comprising (v) interrogating the container with a detection device (e.g., a Raman spectrometer through the window). In some instances, such a process allows any airborne gases or analytes that have reacted or interacted with the colloid particles to be detected and/or measured.

In a preferred embodiment, the vessel is an ampoule made from blown glass (or any other suitable material). In some embodiments, the filling step comprises cleaning the glass, applying vacuum for a predetermined period, purging with an inert gas for a predetermined period, applying vacuum for a second predetermined period, purging with an inert gas for a second predetermined period; injecting the colloidal solution, and, fusing the ampoule by melting an open access region of the ampoule to close the region and produce an impermeable, sealed vessel. In some instances, the cleaning, purging, and vacuuming steps may be repeated multiple times.

In various detailed embodiments, the breaching step comprises breaking the ampoule. The energy of breaking the ampoule may cause dispersion and distribution of colloid. If the ampoule is made from blown glass, upon breaking glass shards reside on the microfluidic container, causing colloid to wick into the microfluidic portion of the container. In a particular embodiment, the cartridge comprises at least one second container connected to the first container by a constricted path and breaking the ampoule causes shards and colloidal solution to fill the first container. In some embodiments, capillary forces draw the colloidal solution but not the shards through the constriction into the second container. In other embodiments, the absorption and optical measurements take place in the liquid in the second container.

In another embodiment, the vessel is a foil packet and the filling step comprises placing a metal foil on a base with a depression, pressing the foil onto the base forming a dimple or depression, cleaning and purging the metal foil, placing an amount of colloidal solution in the dimple under inert conditions, placing a cover foil over the dimpled foil, and sealing the two foils to contain the colloidal solution in the dimple.

In an aspect, a cartridge for use in a microfluidic system for the detection and/or measurement of ambient gases and/or analytes in a gas or liquid sample is provided. The cartridge comprises a microfluidic chip including at least one microfluidic container with at least one free surface; an optical window for optical interrogation of the microfluidic container; a colloid vessel chamber disposed in proximity to the microfluidic container, wherein the colloid vessel chamber includes a colloid vessel comprising colloidal solution, the colloid solution comprising a liquid and nanostructured particles; and an fluid flow manifold disposed in a configuration suitable to direct a flow of the gas or liquid across the microfluidic chip.

In another aspect, a cartridge for use in a microfluidic system for the detection and/or measurement of one or more analytes in a gas or liquid sample is provided. The cartridge comprises a microfluidic chip comprising at least one microfluidic container with an opening for bringing at least one free surface interface region of a fluid in the microfluidic container in contact with the gas or liquid sample; an optical window in optical communication with at least a portion of the microfluidic container, wherein the optical window is for optical interrogation of the microfluidic container, and wherein the optical window is (i) disposed at or in proximity to the opening, or (ii) downstream of the opening; a vessel chamber in fluid communication with the microfluidic container, wherein the vessel chamber holds a vessel comprising a colloidal solution, wherein the colloidal solution comprises a liquid and Surface enhanced Raman scattering (SERS) probes for the detection of an analyte of the one or more analytes; and a fluid flow manifold that directs a flow of the gas or liquid sample across the opening of the microfluidic chip.

In another aspect, a method for measuring the presence of one or more analytes in a sample is provided. The method comprises providing a cartridge comprising (i) a chip comprising at least one container with at least one free surface, (ii) an optical window optically exposing at least a portion of the container, (iii) a fluid flow manifold that directs the sample over the container, and (iv) a vessel comprising a colloidal solution comprising a liquid and nanostructured particles; placing the cartridge in a measuring system with the optical window aligned with an optical component of the measuring system, wherein the measuring system is for measuring the presence of an analyte among the one or more analytes in the sample; breaching the vessel and directing the colloidal solution from the vessel into the container, wherein the colloidal solution at least partially fills the container; passing the sample over the container with the aid of the fluid flow manifold; and using the measuring system to optically detect and/or measure the interaction or reaction of an analyte among the one or more analytes in the sample with the nanostructured particles.

In another aspect, a process for forming a cartridge for use in a microfluidic system for the detection and/or measurement of ambient gases and/or analytes in a gas or liquid sample is provided. The process comprises providing a cartridge comprising (i) a chip comprising at least one container with at least one free surface, (ii) an optical window optically exposing at least a portion of the container, (iii) a fluid flow manifold that directs the sample over the container, and (iv) a vessel chamber adapted to hold a vessel; and placing the vessel in the vessel chamber, wherein the vessel comprises a colloidal solution comprising a liquid and nanostructured particles.

Additional aspects and advantages of the present disclosure will become more readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the claimed invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." or "FIGS." herein) of which:

FIG. 7A shows an ampoule in a cartridge. FIG. 7B shows the ampoule opened with the aid of a breaking tool.

DETAILED DESCRIPTION

Figure 1:
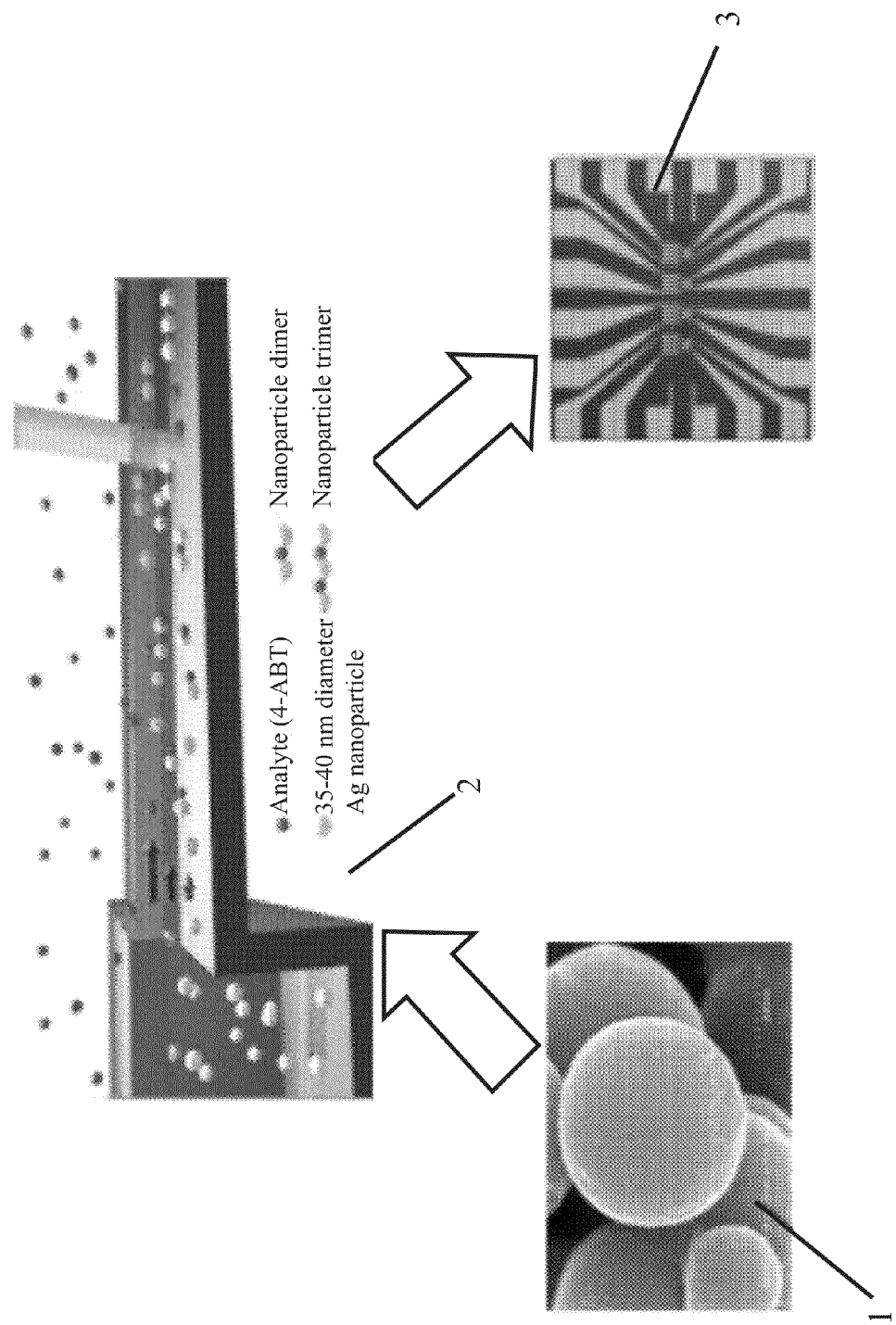
FIG. 1 illustrates the operation of certain embodiments of the microfluidic chip container for the colloidal solution.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanoparticle," as used herein generally refers to a particle having dimensions (e.g., diameter, width, longest dimension) on the order of a few or several nanometers. In some examples, a nanoparticle has dimensions from about 10 nanometers (nm) to 500 nm, or about 20 nm to 200 nm. A nanoparticle can have a dimension from about a few nanometers up to and exceeding a hundred or several hundred nanometers. A nanoparticle may be a nanostructure.

The term "analyte," as used herein, generally refers to a substance whose chemical constituents are being identified, detected or measured. An analyte can be an atom or molecule, or a collection of molecules. An analyte can be provided in a sample that is suspected of containing the analyte.

Raman spectroscopy is a label-free technique for molecular detection and molecular dynamics studies. Surface enhanced Raman scattering (SERS) improves the sensitivity by amplifying the original Raman scattering intensity for several or even tens of orders of magnitude. Spherical gold and silver nanoparticles have been used as substrates in SERS-based molecule detections due to their advantages in local scattering field enhancing, surface chemical modifications, biocompatibility, and well-established chemical synthesis processes. The intrinsic plasmon resonance of single nanoparticles and the plasmon coupling between adjacent nanoparticles are conditions for local field enhancing. The optimal SERS substrate of nanoparticle assemblies depends on the size, the local dielectric environment and the interparticle distance. SERS spectroscopy shows chemical-bond information, and is a useful method for label-free biomolecular imaging.

Nanoparticles are useful, in part, because of their unique, highly desirable properties that makes a superior detection platform for life science research, in vitro diagnostic testing, and in vivo imaging. One such property of nanoparticles is the increased intensity of Raman scattering which they contribute to the measurement of analyte species by Raman spectroscopy. The increased intensity results from the high density of SERS-active sites the nanoparticles contribute to the system. Other structures such as nanotips and nanorings have also been demonstrated for use in high resolution SERS spectroscopy and imaging. These structures provide significant field enhancement in experiments and in simulations.

Microfluidics is a field of work that deals with the fluid-based transport of mass, momentum, or energy. Microfluidic channels are completely enclosed and not in direct communication with the surrounding atmosphere.

Analyte Detection

This disclosure provides devices, systems and methods for bringing an analyte in contact with a fluid containing particles that aid in detecting the analyte. In some cases, analyte detection is optical, though other forms of analyte detection are possible, such as electrochemical or electrostatic.

Techniques for label-free single molecule level detection and recognition of specific molecules or biomolecules are important in defense, medical, and environmental sensing applications. Under optical excitation of an analyte with a given frequency, a metallic nanostructure can sustain a plasmon resonance that results in highly enhanced local electromagnetic fields and distinct spectral extinction characteristics.

For sensing or detection applications, the field enhancement can be utilized for surface-enhanced Raman spectroscopy (SERS), and spectral extinction characteristics can be used to detect the changes in local refractive index. The plasmon resonance characteristic depends on the topology of each nanostructure.

Normal Raman scattering may be a scattering process in which photons incident on a sample transfer energy to or from the sample's vibrational or rotational modes. Individual bands in a Raman spectrum may be characteristic of specific molecular motions. As a result, each of a plurality of analytes can have its own unique Raman signature. When a Raman-active molecule is positioned within an electromagnetic field generated upon excitation of the localized surface-plasmon resonance of a nanostructure, the Raman signal may increase by multiple folds of magnitude.

Raman imaging of living cells can nondestructively probe the intracellular biochemical dynamics without prior fluorescent or radioactive labeling, but the formidably low efficiency of Raman scattering hinders its applications in the detection of molecules at micromolar or lower concentrations. However, SERS by metallic nanostructures can increase the original Raman scattering intensity many orders of magnitude, which makes the Raman detection of low concentration molecules practical.

SERS is a process in which the Raman scattering signal is increased when a Raman-active molecule is spatially confined within range of the electromagnetic fields generated, in some cases, upon excitation of the localized surface plasmon resonance of nanostructured metal surfaces. Both chemical and conformational information can be elucidated from SERS. SERS possesses many desirable characteristics as a tool for the chemical analysis of molecular species including high specificity, attomole to high zeptomole mass sensitivity, micromolar to picomolar concentration sensitivity, and interfacial generality.

Devices, systems and methods of the disclosure can use probes (e.g., particles, nanoparticles) that form complexes with one or more analytes in a sample under interrogation. The probes can be used in SERS-based detection. In some examples, during use of a device for analyte detection, when an analyte first interacts with a SERS-active probe particle, a monomer may be formed that provides surfaced-enhanced amplification of a signal. Monomers can aggregate into dimers that include two or more SERS-active particles sandwiching the analyte, which can increase SERS amplification by several orders of magnitude.

Devices

This disclosure provides devices for detecting analytes. In some examples, analytes are detected with the aid of a SERS-based detection system. A SERS-based detection system can enable for the detection of one or more analytes in a gas or liquid sample, such as, for example, an air sample.

Devices of the disclosure can include at least one free surface interface region, which can include an interface between two phases, such as a gas and a liquid, or a first liquid and a second liquid. In some examples, a free surface interface region is an air-liquid interface. A free surface interface region can have dimensions such that a fluid in the at least one free-surface interface region is confined by surface tension. In some examples, the free surface interface region comprises cross section dimensions from about 50 nm to 1 mm, and a length from about 1 micrometer to 10 cm. Various features of the free surface interface region may be as described in U.S. Pat. No. 8,017,408 to Meinhart et al. ("Device and methods of detection of airborne agents"), which is entirely incorporated herein by reference.

In some examples, a system for detecting one or more analytes comprises a microfluidic device having a free-surface interface region. A fluid interacts with analytes in a sample that comes into contact with the fluid, and analytes in the sample are absorbed into the fluid. The microfluidic device includes an excitation region (or area) and a detection region (or area). In the excitation region, an electromagnetic energy may excite a probe (e.g., SERS probe) in the fluid containing analytes. An emitted spectra is detected by a detection device in optical communication with the detection region. The excitation region and the detection region can be the same region. The free-surface interface region can be in fluid communication with the excitation and detection regions.

The system further includes an electromagnetic energy source that directs electromagnetic radiation at the excitation region, and a detector that detects the emission spectra from excited SERS probes in the detection region.

FIG. 1 shows a colloidal solution 1 of particles injected into a microfluidic container 2. In some examples, the particles are nanoparticles. Airborne reagents that have an absorption affinity for the liquid of the solution can be absorbed, and some can bind with the particles. These reagent/particle groups can be readily detected and spectrally analyzed optically due to the SERS effect. The desirable size for such a container, due to a variety of reasons, including surface-to-volume ratio, optical penetration depths and others, turns out to be on the order of several micrometers ("microns") in length and width and on the order of 1 micron or less in depth. Such containers are best made using microlithographic techniques on a chip 3. This microfluidic chip is an important element of the techniques described herein. Similar chip variants in terms of manufacturing techniques for a flow channel variant of a container 2 can be as described, for example, in U.S. Pat. No. 8,017,408, which is entirely incorporated herein by reference.

In an example, with reference to FIG. 1, the container 2 includes 35 nanometer (nm) to 40 nm silver particles in a colloidal solution. A free surface interface region of the container 2 (top portion of middle figure) comes in contact with an analyte in a vapor phase sample. The analyte enters the solution and interact with the silver particles to form, for example, analyte-particle monomers, dimers and/or trimers. The analyte-particle subunits are then detected via the SERS effect, as described, for example, in U.S. Pat. No. 8,017,408, which is entirely incorporated herein by reference.

Generally, one measurement cycle comprises releasing fluid into the open surface microfluidic container on the chip, and allowing for a period of absorption and detection. For many measurement scenarios, once this period is complete, the chip and fluid may be disposable, as cleaning and reusing may not be practical.

In some embodiments, both the fluid and particles (e.g., nanostructures, nanoparticles) are clean and contaminant free at the start of the measurement period. For larger systems, it is practical to install a new chip and insert the solution, often a colloidal suspension of particles (e.g., nanoparticles), into the chip at the time of measurement with external microfluidic plumbing. However for field portable applications requiring simplicity and ruggedness, such plumbing may not be desirable. For such systems, the delivery of fresh, clean colloidal solution to the measurement site has been problematic. Mixing and delivering on site is not possible for many applications of the technology.

Figure 2:
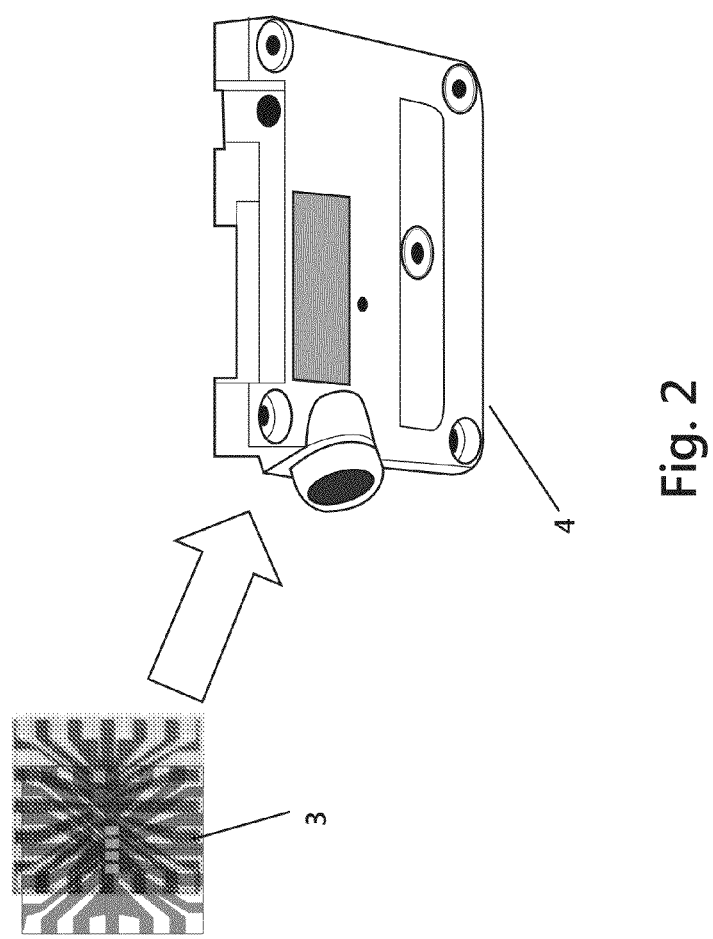
FIG. 2 illustrates certain embodiments of the chip in relation to the cartridge.
Figure 3:
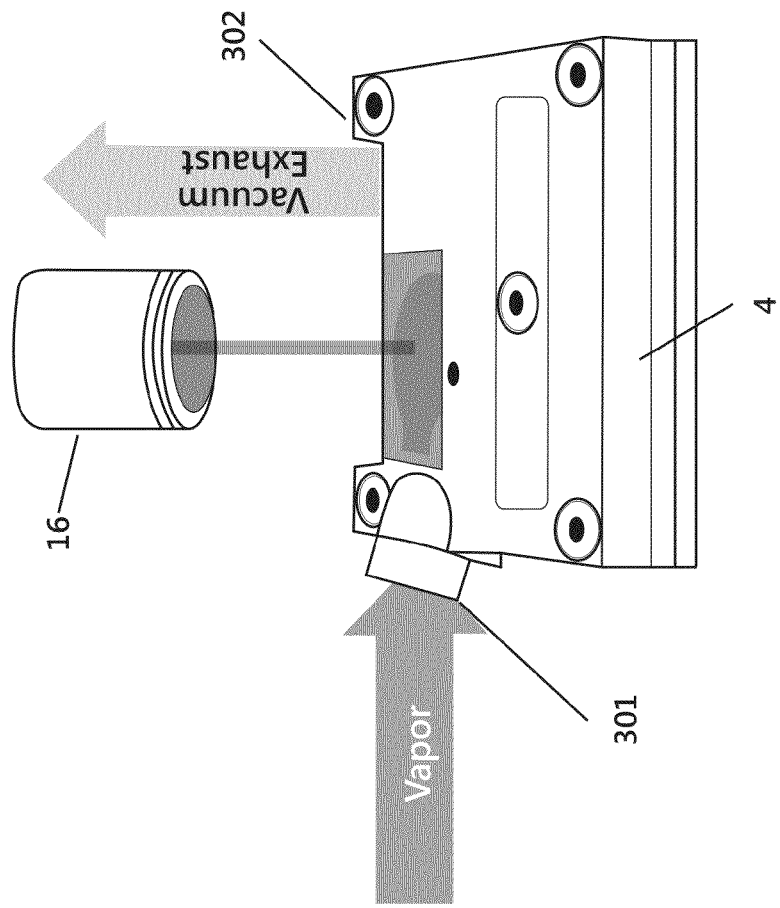
FIG. 3 illustrates certain embodiments of the cartridge in measurement mode.

As shown in FIGS. 2 and 3, the microfluidic chip 3 can be installed in a cartridge 4, which contains a supply of clean colloidal solution, and further includes provision for airflow and exhaust as well as optical interrogation 16. The cartridge 4 can include an inlet port 301 for permitting a sample (e.g., gas or vapor) to enter the cartridge, and an outlet (or exhaust) port 302 for permitting the sample to leave the cartridge 4. In some examples, the cartridge 4 can have a length from about 0.5 inches to 6 inches, or 1 inch to 3 inches; a width from about 0.5 inches to 6 inches, or 0.5 inches and 3 inches; and a thickness from about 0.1 inches to 6 inches, or 0.5 inches and 3 inches.

Figure 4A:
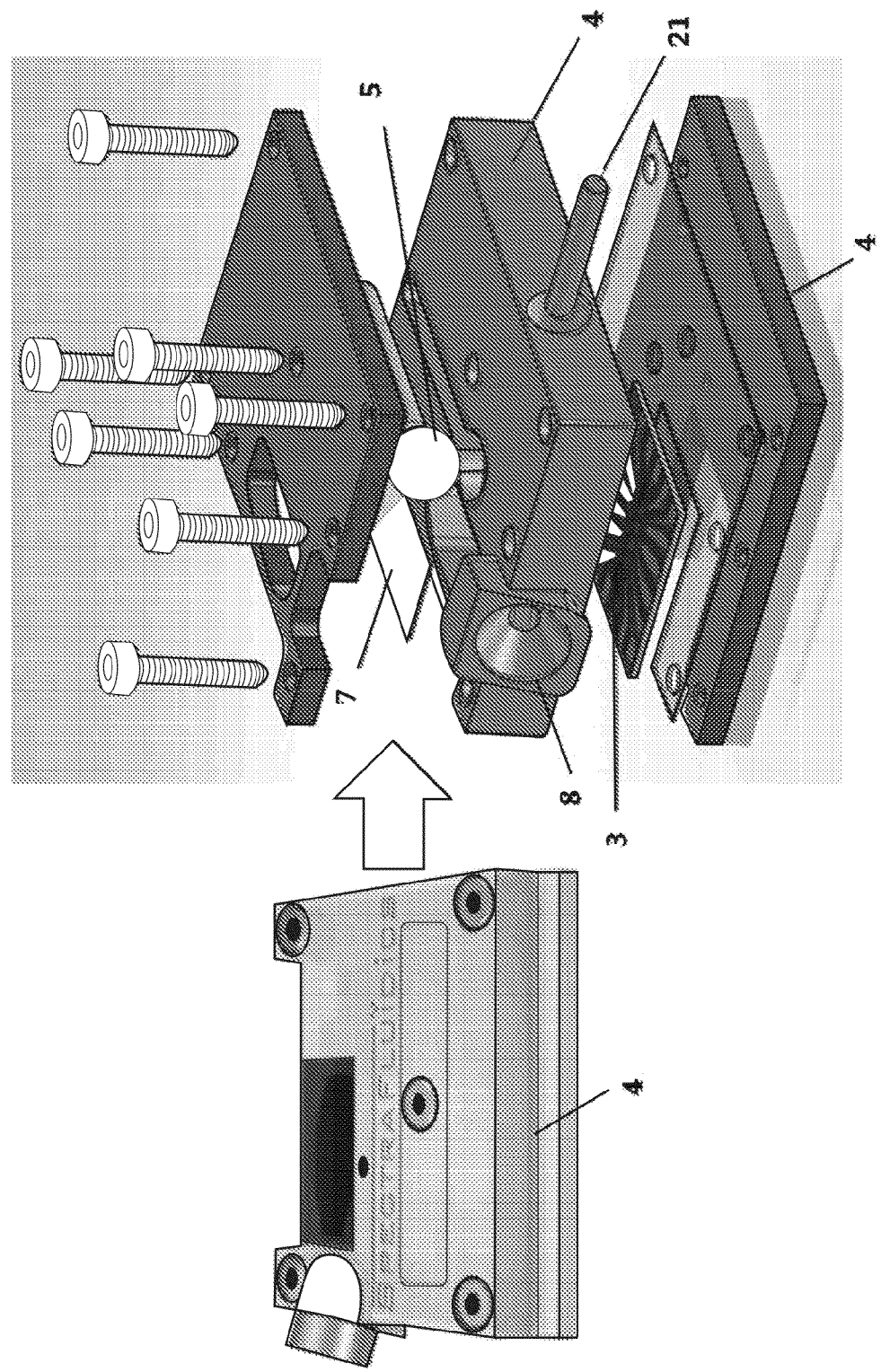
FIGS. 4A and 4B show schematic perspective and top views, respectively, of the elements of certain embodiments of the cartridge.
Figure 4B:
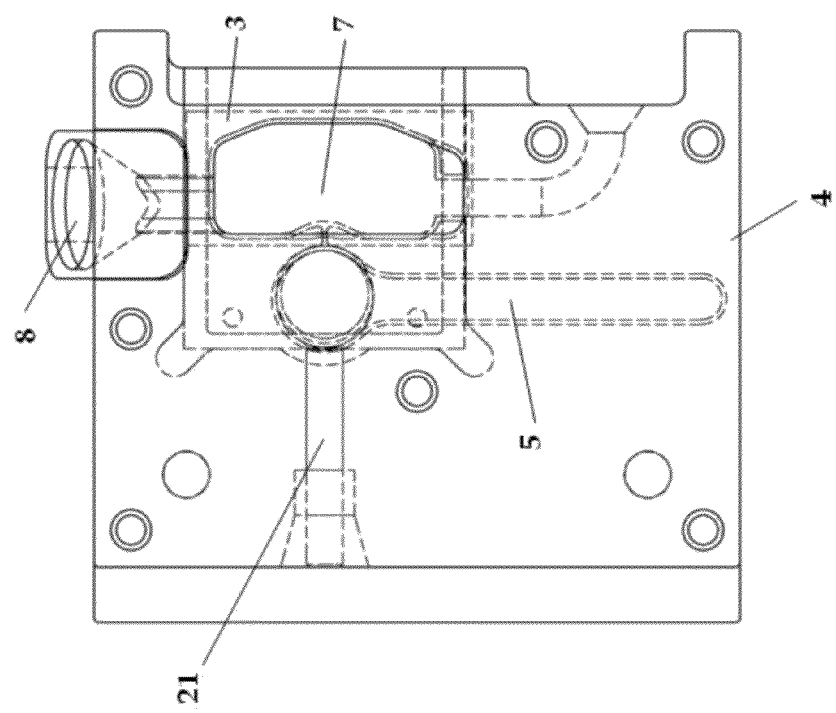
Figure 5:
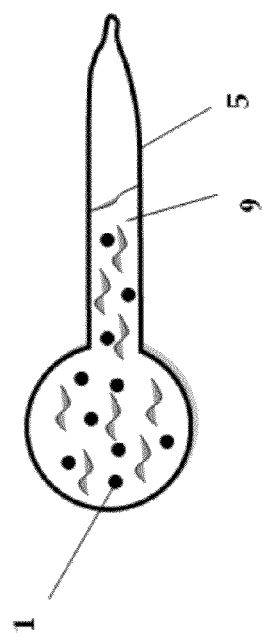
FIG. 5 is a schematic of certain embodiments of an ampoule.

In FIGS. 4A and 4B, some details are shown of cartridge 4. In some examples, chip 3 is mounted under an optical window 7 and the space over the chip is exposed to an airflow manifold 8. In some embodiments, an important element in the cartridge is the reservoir of colloidal solution, a novel colloid storage vessel. In one embodiment the vessel is an ampoule 5. The ampoule 5 can be a sealed glass capsule, in some cases containing a liquid, such as, for example, a colloidal solution. FIG. 5 schematically illustrates an example ampoule 5. The ampoule 5 contains a selected fluid 9 with suspended particles 1. In some situations, the probe particles 1 can be nanoparticles 1. The probe particles 1 can be functionalized particles, such as functionalized nanoparticles. In some examples, the particles 1 are nanoparticles formed of gold, silver, or combinations thereof.

The cartridge 4 includes a breaking tool 21 for coming in contact with the ampoule 5 and breaking at least a portion of the ampoule. This enables a user to release the contents of the ampoule 5 during use of the cartridge 4. The breaking tool 21 can be spring loaded or include a mechanical actuation mechanism for directing the breaking tool 21 to the ampoule.

The cartridge 4 can contain all of the system elements needed to perform a SERS measurement on airborne reagent other than the spectrometer and an airflow mechanism. In some embodiments, the cartridge is used on a per measurement basis and is disposed of or refurbished after each use. This arrangement makes practical, ready to use, rugged and reliable field systems utilizing the SERS technique.

The cartridge 4 can be inserted or otherwise disposed in a system with the spectrometer (e.g., Raman spectrometer) for detection of one or more analytes in a sample directed through the cartridge 4. The system can be a portable system, or a system that is adapted to be fixed at a particular location.

The cartridge 4 can include ribbed or corrugated surfaces on one or more surfaces of the cartridge to enable a user to grip the cartridge 4. The cartridge 4 can include features (e.g., grooves or depressions) to enable the cartridge to mate with a holder of the system.

Some embodiments describe the preparation and operation of the ampoule 5. In some embodiments, the preparation and operation of the ampoule 5 is important to the success of the measurement, and thus, the utility of the cartridge approach. A preferred implementation of the ampoule and the process of using it are as follows.

The ampoule 5 can be formed of a transparent material, such as silicon oxide (e.g., $SiO_2$) or a polymeric material. In some cases, the ampoule 5 can be made from blown glass, and can comprise a spherical vessel and a fill tube. In certain embodiments, the size of the vessel of the ampoule 5 that is appropriate for this application is a spherical vessel on the order of micrometers ("microns") to a few mm in diameter. The spherical vessel (e.g., of the ampoule) can have a diameter from about 500 microns to 1000 mm, 1 mm to 15 mm, or 1 mm to 10 mm. The fill tube may be of any suitable or convenient length. The spherical vessel can have a length from about 0.1 cm to 40 cm, 0.5 cm to 20 cm, or 0.5 cm to 5 cm.

Figure 6:
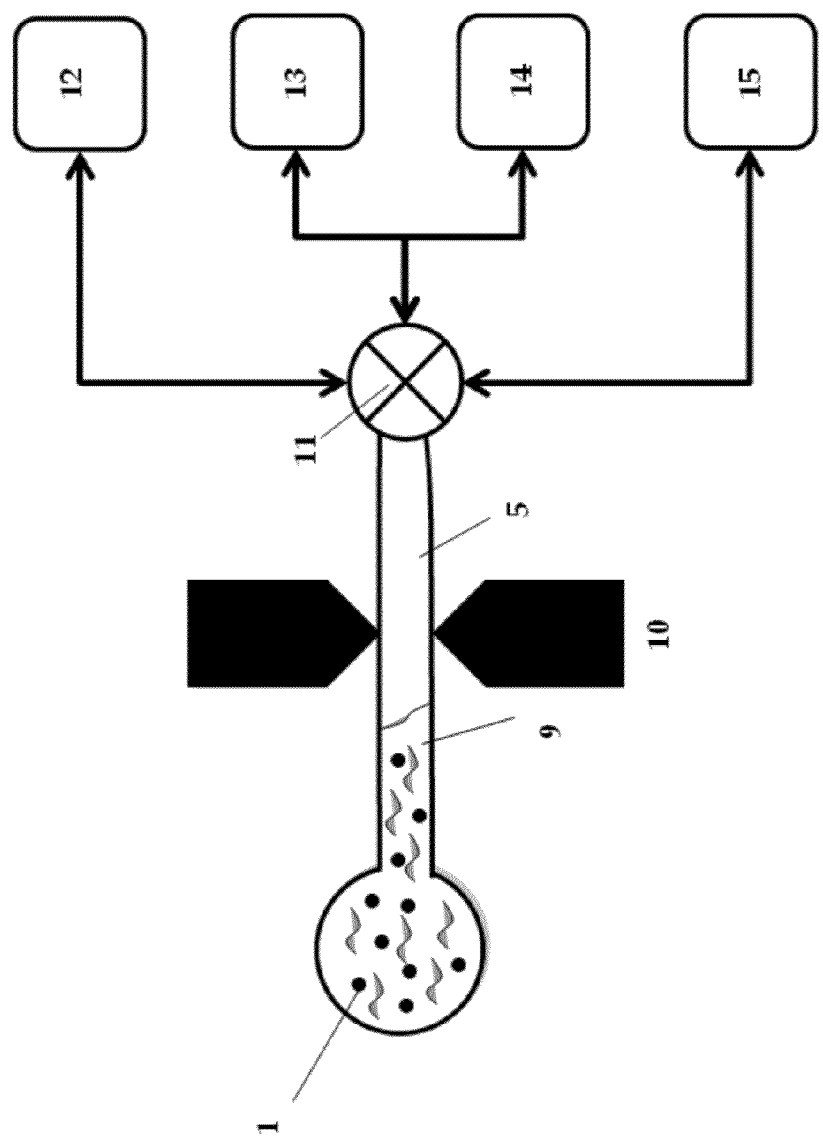
FIG. 6 shows schematically an ampoule filling process according to one embodiment.

FIG. 6 shows a setup and an approach for preparing the ampoule 5. The fill tube of the ampoule 5 is connected to a mixing device 11 connected to various appropriate sources 12-15. Such a device is known in laboratory environments as a Schlenk. In some instances, sources 12-15 may include a cleaning solution, an inert gas (e.g., Ar, He) source, a vacuum source and a reservoir of the desired colloidal solution. A series of clean/purge/vacuum steps can be repeated until the ampoule 5 is decontaminated. In some examples, the ampoule is injected with colloidal solution (liquid 9 and particles 1). Following injection with colloidal solution, the fill tube can be fused 10, closing off the ampoule and creating a contaminant free, substantially sealed reservoir of colloidal solution. In some embodiments, a suitable tip off length is on the order of several mm to several cm.

With reference to FIG. 7A, ampoule 5 is mounted in the cartridge 4 in a first chamber 701 that is in fluid communication with a second chamber 702 through a fluid passageway 703. The second chamber 702 can be a microfluidic container. With reference to FIG. 7B, when a user wishes to use the cartridge 4 to make a measurement for an analyte, the ampoule 5 can be opened with the aid of a breaking tool (e.g., breaking tool 21 in FIGS. 7A and 7B). In an example, the user manually presses the breaking tool 21 into the ampoule 5. In another example, movement of the breaking tool is regulated with the aid of an actuator or spring-loaded mechanism, and the user can engage the breaking tool 21 with the ampoule 5 to open the ampoule 5 using the actuator or spring-loaded mechanism. In some examples, the breaking tool 21 can be used to form of a punch, which may shatter at least a portion of the ampoule 5, to release the contents of the ampoule 5 into the first chamber 701.

Various types of breaking tools are possible. In some cases, the breaking tool can be an electrical, acoustical, mechanical device, electromechanical, optical and/or thermal. In some examples, the punch may be provided through a mechanical or acoustical device. The shattering energy can splatter the solution and ampoule shards into the first chamber 701. In some embodiments, the wicking of the liquid to the shards aids in transporting the liquid content of the ampoule 5 into the second chamber 702.

The chip 3 can be housed (or disposed) in the cartridge 4 (see, e.g., FIGS. 4A and 4B). In some examples, the first chamber 701, second chamber 702 and passageway 703 are at least partially defined by the chip 3 and the walls of structures of the cartridge. The first chamber 701, second chamber 702 and passageway 703 are formed upon the chip 3 being inserted into the cartridge 4.

In some embodiments, there are two chambers formed by the chip 3 and cartridge 4, the first chamber 701 and the second chamber 702, which are fluidically connected by the constricted passageway 703. As an alternative, the liquid and shards are scattered into the first chamber 701, and capillary action draws the fluid, but not the shards, into the second container, which is optically accessible 7 to the spectrometer. In some situations, a filter can be provided in the passage 703 to permit fluid to flow through the passage 703 from the first chamber 701 to the second chamber 702, but prevent shards from flowing from the first chamber 701 to the second chamber 702.

In some examples, the passageway 703 has a diameter from about 500 nanometers and 2 micrometers. The cartridge 4 can be formed of a polymeric material, such as polytetrafluoroethylene (PTFE) or perfluoroalkoxy (PFA).

As described elsewhere herein, colloid storage and delivery in the microfluidic cartridge can utilize an ampoule, which can be an glass ampoule. In another embodiment, the glass ampoule contains the appropriate amount of colloid and delivers the colloid to the microfluidic chip by breaking the ampoule. An alternative approach for storing and delivering the colloid involves the use of a "Colloid Packet", constructed of metal foil, polymer film, or a layered combination of the two. A colloid packet can include a hemispherical dimple or depression constructed of the given material of construction, topped by a flat cover sheet. The hemispherical depression can allow for storage of the colloid while the flat cover sheet is used to seal the system. Ultrasonic welding of the hemispherical depression and the cover sheet can allow the system to be autogenously welded without the use of solder or adhesives, which may negatively affect the colloid stability/lifetime. In other embodiments, the colloid packet lends itself to automated production, which may result in decreased production time and costs and increased scalability to high volumes. Automated production may also aid in maintaining quality control.

Figure 8:
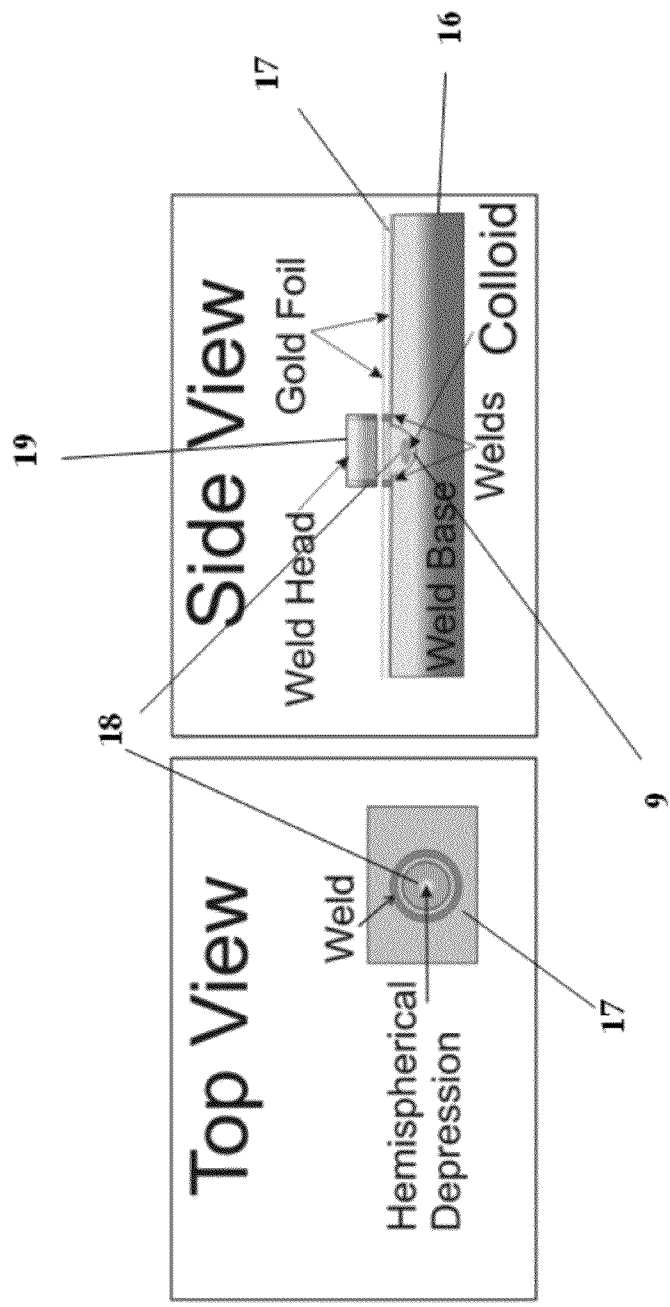
FIG. 8 illustrates an embodiment of a "colloid package".

FIG. 8 depicts a non-limiting example of a "colloid packet" implementation. A gold foil 17 (or other inert material) is placed in a welding base 16. The base can have a dimpled region, and when the gold foil 17 is pressed on to the base 16, a depression or dimple 18 is formed in the foil. This surface may be cleaned and purged as necessary. The dimple 18 may have a size (e.g., diameter, longest dimension) from about 1 millimeter (mm) to 60 mm, or 1 mm to 30 mm, or 1 mm to 15 mm. A drop of colloid 9 can then be placed in the depression 18 and a covering foil can be placed over the first foil. In some instances, these operations are preferably done in a clean inert gas environment (or under vacuum) to maintain purity of the colloid. In an example, a welder 19 then seals the dimple and a packet containing colloid is formed. The packet can be a sealed packet, such as, for example, a hermetically sealed packet. Such a packet may be utilized in a cartridge for analyte detection, as described elsewhere herein (see, e.g., FIGS. 4A and 4B). Breaking the packet, particularly in such a fashion to insure acceptable dispersion of the colloid into the container, may be accomplished in a variety of ways that will be apparent to one skilled in the art. For example, the packet may be sealed at an over pressure, and a sharp object (e.g., a needle) may be used to burst the packet, akin to puncturing a balloon, spraying the colloid into the surrounding region including the container area.

This disclosure describes a cartridge, ampoule, ampoule filling and preparation, and colloid delivery to a chip that may be rugged, contaminant free, disposable measurement platform for SERS based instruments. Systems, devices, and methods described herein provide various features and benefits, such as, for example a cartridge that houses a microfluidic chip for analyte detection. The cartridge can protect the chip from the environment during storage. Another feature or benefit of systems of the disclosure is the storage of a colloidal solution in an ampoule or other storage vessel, which protects the colloidal solution and maintains purity during storage and releases it to the chip when a test (e.g., analyte detection) is initiated. Systems provided herein enable for the delivery of a colloid, which enables for the delivery of the colloid from the vessel (e.g., ampoule) to the chip container or reservoir when the test is initiated. Such storage and delivery approaches for a colloidal solution can block an air stream from interacting with the colloid before it enters a container of the cartridge when the test is initiated.

Apart from protection, the cartridge can provide various processing benefits. For example, the cartridge can control or regulate fluid flow (e.g., air flow) through a manifold and direct fluid flow over a microfluidic container situated in the cartridge. The cartridge can be designed or configured for easy and low cost manufacturing—machined or injection molded/stamped metal. The cartridge can be formed of inert materials, such as polymeric materials. Examples of mpolymeric materials include, without limitation, polytetrafluoroethylene (PTFE) and perfluoroalkoxy (PFA). Metal surroundings, which may form a casing of the cartridge, may be aluminum or stainless steel, or other inert metals. Metal components of the cartridge can be formed of aluminum or stainless steel, or inert metals, such as, for example, Ag, Au, Pt, or combinations thereof. A cartridge can include multiple interfaces for connection to an instrument (or system) for analyte detection. For instance, an optical interface of the cartridge can enable excitation energy (e.g., Raman excitation source) to be directed into the cartridge and come in contact with the analyte and colloidal solution, and an optical signal scattered from the solution to be detected by a detector (e.g., Raman detector) of the system.

A system for analyte detection can include a chip and an instrument with optics for analyte detection. The instrument can include a thermoelectric (TE) device for regulating a temperature of the cartridge and a colloidal solution in a storage vessel disposed in the cartridge. The TE device can be situated below the chip. The chip can include electrical contacts on a side of the chip, which can provide for, for example, power to and control of the TE device, and/or power to and control of one or more sensors, including, without limitation, a humidity sensor and/or a temperature sensor. In some cases, the chip includes a window or other optical interface on a top portion of the chip, which is adapted to enable excitation light to enter the chip and scattered light from be directed out of the chip and into an optical detector. The chip can include a fluid flow (e.g., airflow) manifold comprising an inlet to provide a fluid stream into the chip, and an outlet in fluid communication with a pumping system comprising one or more pumps. The fluid stream (e.g., air stream) can include (or be suspected to include) one or more analyte.

In some cases, the fluid stream is permitted to come in contact with the colloidal solution at a free surface interface region of the microfluidic chip in the cartridge. Portions of the cartridge can be sealed such that the fluid stream does not leak into the colloid container and come in contact with the colloidal solution.

Some embodiments provided herein describe a combination of devices and processes with practical and valuable application of SERS based detection systems for field use.

In the foregoing description, a cartridge has been described for the case where the liquid medium is a colloidal solution of nanoparticles, and the analysis method includes but is not limited to optical means such as spectrometers. The basic concepts disclosed herein also apply to other measurement techniques and are not limited to SERS-based techniques. Such other measurement techniques may rely on delivering a liquid medium of a desired type, exposing it to ambient atmosphere to capture analytes, and detecting the analytes with a radiation source, chemical techniques, or other known analyte characterization methodologies. In some embodiments, with a different liquid media filling the vessel, the cartridge concept applies to any detection device that detects the presence of analyte species by a method selected from the group consisting of Raman spectroscopy or SERS measurements on a substrate fixed to the microchannel walls or in the bulk liquid solution contained within the microchannel, electrochemical analysis techniques, fluorescent chemical marker techniques, fluorescence quenching, redox-labeled nucleic acid binding, and techniques including, but not limited to, the molecules deoxyribonucleic acid (DNA), ribonucleic acid (RNA) and peptide nucleic acid (PNA), and techniques that employ x-ray absorption, infrared (IR) light, visible light, ultraviolet (UV) light, and other electromagnetic radiation absorption techniques, mass spectroscopy techniques, liquid chromatography techniques, flame ionization analysis techniques, DNA melting point techniques, and titration analysis techniques.

Devices, systems and methods of the disclosure can be combined with or modified by other devices, systems and methods, such as, for example, those described in Patent Cooperation Treaty (PCT) Application Nos. PCT/US2010/34127, PCT/US2010/45761, PCT/US2010/052742, PCT/US2010/58234, PCT/US2011/059213; U.S. patent application Ser. No. 13/289,679; and U.S. Pat. No. 8,017,408, each of which is incorporated herein by reference in its entirety.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A system for detecting analytes, the system comprising:
a cartridge formed from an inert polymeric material, the cartridge having a vapor inlet port to an airflow manifold and a vacuum exhaust port from the manifold;
a microfluidic chip installed in a first chamber of the cartridge, the chip exposed to the airflow manifold and the chip including at least one microfluidic container with at least one free surface;
an optical window in the cartridge for optical interrogation of the microfluidic container; and,
a colloid vessel disposed in a second chamber of the cartridge, the colloid vessel containing a colloidal solution comprising Surface Enhanced Raman Scattering (SERS) probes in a liquid, and the second chamber being in fluid communication with the first chamber via a fluid passageway.

2. The system of claim 1, wherein the colloid vessel is a glass ampoule.

3. The system of claim 2, the cartridge having an access port disposed to allow a vessel breaking tool to break the glass ampoule, and the fluid passageway being constricted such that upon breaking of the ampoule capillary forces draw the colloidal solution, but not glass shards of the ampoule, through the constricted passageway to the microfluidic container.

4. The system of claim 1, wherein the colloid vessel is a metal foil packet with size from about 1 mm to 15 mm.

5. The system of claim 4, the cartridge having an access port disposed to allow a vessel breaking tool to puncture the metal foil packet such that upon puncturing of the foil packet colloidal solution flows through the fluid passageway to the microfluidic container.

6. The system of claim 1, the SERS probes being nanostructured particles.

7. The system of claim 1, the inert polymeric material being polytetrafluoroethylene (PTFE).

8. The system of claim 1, the inert polymeric material being perfluoroalkoxy (PFA).

9. The system of claim 1, the cartridge including ribbed or corrugated surfaces to enable a user to grip it.

* * * * *